United States Patent [19]

Lang et al.

[11] Patent Number: 4,539,320

[45] Date of Patent: Sep. 3, 1985

[54] HUMECTANT COMPOSITIONS CONTAINING THIAMORPHOLINONE OR A DERIVATIVE THEREOF

[75] Inventors: Gérard Lang, Epinay-sur-Seine; Jean Maignan, Tremblay Les Gonesse; Jean-Luc Leveque, Paris; Laurent Rasseneur, Thorigny-sur-Marne, all of France

[73] Assignee: Societe Anonyme dite: L'Oreal, Paris, France

[21] Appl. No.: 484,604

[22] Filed: Apr. 13, 1983

[30] Foreign Application Priority Data

Apr. 15, 1982 [FR] France .................. 82 06499

[51] Int. Cl.³ .................................... A61K 31/54
[52] U.S. Cl. .......................................... 514/222
[58] Field of Search ................ 544/58.2; 424/63, 70, 424/246, 168

[56] References Cited

U.S. PATENT DOCUMENTS 2,755,278  7/1956  Goldberg et al. .................. 544/58.2

FOREIGN PATENT DOCUMENTS 1288907  2/1961  France .
4120827  12/1966  Japan .................. 544/58.2

OTHER PUBLICATIONS

Lehr et al., *J. Med. Chem.*, vol. 6, No. 2, pp. 136–141, Mar. 1983.
Chem. Abstracts 84:105613q (1976).
Chem. Abs. 80:146182j (1974).
Bushey et al., *J. Org. Chem.*, vol. 45, No. 21, pp. 4198–4206, Oct. 1980.
Chem. Abs. 71:3392f (1969).
Chem. Abs. 84:35211f (1976).

*Primary Examiner*—Sidney Marantz
*Assistant Examiner*—Shawn P. Foley
*Attorney, Agent, or Firm*—Cushman, Darby & Cushman

[57] ABSTRACT

A composition for topical application to the skin comprises, in an appropriate cosmetic vehicle, as an active agent, a compound of the formula

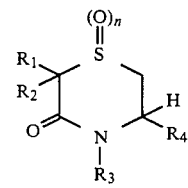

wherein, $R_1$ and $R_2$ represent hydrogen or lower alkyl; $R_3$ represents hydrogen, alkyl containing 1–4 carbon atoms, mono- or polyhydroxyalkyl having 2–16 carbon atoms, carbamylalkyl, carboxyalkyl or alkoxycarbonylalkyl; $R_4$ represents hydrogen or —$COOR_5$ represents hydrogen, alkyl having 1–18 carbon atoms optionally interrupted by one or more hetero atoms, or mono- or polyhydroxyalkyl having 2–18 carbon atoms; and n is 0 or 1.

This composition improves the elasticity and suppleness of the skin.

3 Claims, No Drawings

HUMECTANT COMPOSITIONS CONTAINING THIAMORPHOLINONE OR A DERIVATIVE THEREOF

The present invention relates to a composition for the skin comprising, as the active component, thiamorpholinone or a derivative thereof.

Active components capable of imparting to the skin good elasticity and good suppleness are generally components called "humectants", which also prevent the drying out of the compositions principally in the form of creams, during storage and use.

Very few humectants, with the exception, however, of sodium lactate, are capable of exercising this dual action and in particular, good hydration of the skin.

Representative other known humectant agents, which are the most currently employed, include sodium pyrrolidone carboxylate, polyols such as glycerine, sorbitol and propylene glycol as well as other substances such as urea.

These hygroscopic substances, if they absorb the humidity of ambient air and maintain the water content of the compositions, disadvantageously they only achieve, for the most part, average and time limited effects with regard to the suppleness and elasticity of the skin.

After numerous studies of various classes of compounds, it has now been found that these particularly desirable properties can be obtained by employing thiamorpholinone or one of its substituted derivatives.

In effect, it has been established that compositions containing such compounds impart to the skin particularly long lasting suppleness and excellent elasticity.

The comparative tests carried out using the apparatus described in French Pat. No. 78,25149 have confirmed that the compositions of the present invention possess these excellent properties.

The present invention thus relates to, as a new industrial product, a composition for topical application to the skin comprising, in an appropriate cosmetic vehicle or carrier, as an active agent for imparting elasticity and suppleness to the skin, an effective amount of at least one compound having the formula

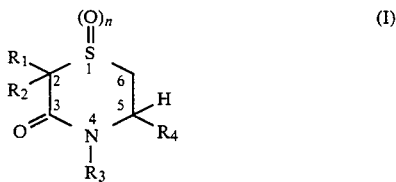

wherein $R_1$ and $R_2$ each independently represent hydrogen or lower alkyl having 1-4 carbon atoms, $R_3$ represents hydrogen, linear or branched alkyl having 1-4 carbon atoms, mono- or polyhydroxyalkyl having 2-16 carbon atoms, carbamylalkyl, carboxyalkyl or alkoxycarbonylalkyl wherein the alkyl moiety of each contains 1-17 carbon atoms and the alkoxy moiety contains 1-3 carbon atoms, $R_4$ represents hydrogen, lower alkyl having 1-4 carbon atoms or —$COOR_5$ wherein $R_5$ represents hydrogen, alkyl having 1-18 carbon atoms, optionally interrupted by one or more heteroatoms such as oxygen, or mono or polyhydroxyalkyl having 2-18 carbon atoms, and n is 0 or 1.

Representative compounds corresponding to Formula I include, particularly:

(1) 3-thiamorpholinone,
(2) 1-oxo-3-thiamorpholinone,
(3) 2-methyl-3-thiamorpholinone,
(4) 2-methyl-1-oxo-3-thiamorpholinone,
(5) 2,2-dimethyl-3-thiamorpholinone,
(6) 2,2-dimethyl-1-oxo-3-thiamorpholinone,
(7) 4-ethyl-3-thiamorpholinone,
(8) 3-thiamorpholinone-5-carboxylic acid,
(9) 1-oxo-3-thiamorpholinone-5-carboxylic acid,
(10) 2-methyl-3-thiamorpholinone-5-carboxylic acid,
(11) 2-methyl-1-oxo-3-thiamorpholinone-5-carboxylic acid,
(12) 2,2-dimethyl-3-thiamorpholinone-5-carboxylic acid,
(13) 2,2-dimethyl-1-oxo-3-thiamorpholinone-5-carboxylic acid,
(14) 4-(2-hydroxyethyl)-3-thiamorpholinone,
(15) 4-(2-hydroxyethyl)-1-oxo-3-thiamorpholinone,
(16) 4-(2-hydroxypropyl)-3-thiamorpholinone,
(17) 4-(2,3-dihydroxypropyl)-3-thiamorpholinone,
(18) 3-thiamorpholinone-5-n-octyl carboxylate,
(19) 3-thiamorpholinone-5-n-decyl carboxylate,
(20) 3-thiamorpholinone-5-n-dodecyl carboxylate,
(21) 3-thiamorpholinone-5-(2 ethyl)hexyl carboxylate,
(22) 3-thiamorpholinone-5-n-tetradecyl carboxylate,
(23) 3-thiamorpholinone-5-n-hexadecyl carboxylate,
(24) 3-thiamorpholinone-5-(2-hydroxy)propyl carboxylate,
(25) 3-thiamorpholinone-5-(2,3-dihydroxy)propyl carboxylate,
(26) 4-(ethoxycarbonylethyl)-3-thiamorpholinone,
(27) 4-(methoxycarbonylmethyl)-3-thiamorpholinone,
(28) 4-(2-ethoxycarbonylethyl)-3-thiamorpholinone,
(29) 4-(1-ethoxycarbonylethyl)-3-thiamorpholinone,
(30) 4-(carboxymethyl)-3-thiamorpholinone,
(31) 4-(2-carboxyethyl)-3-thiamorpholinone,
(32) 4-(1-carboxyethyl)-3-thiamorpholinone, and
(33) 4-(carbamylmethyl)-3-thiamorpholinone.

Certain ones of these compounds are known, principally compounds: (1), (2), (3), (5) and (7) above, which are described by H. Lerh, Col. J. Med. Chem., 1963, 6, page 136. Also Compound (8) is described in French Pat. No. 1,288,907.

The other compounds are new and various processes for their preparation are given below.

The compositions, according to the present invention, generally contain from 0.1 to 20 weight percent of at least one compound of Formula I, but preferably from 2 to 12 weight percent, based on the total weight of the composition.

The compositions of the present invention can be provided in various forms such as, for example, lotions, creams for the care of the face, body milks, makeup remover milks or creams, sunscreen milks or creams, complexion foundations, complexion creams, makeup bases, anti-wrinkle creams or creams for the outline of the eyes, masks, liquid soaps, bath foams and the like.

In accordance with the invention, the compositions can also contain, in combination with the active agent of Formula I, a conventional cosmetic agent such as for example, glycerol, urea, salicylic acid, pyrrolidone carboxylic acid, lactic acid or a salt of these acids.

The new compounds included in Formula I in which the radical $R_3$ is other than hydrogen are obtained in accordance with the following reaction scheme:

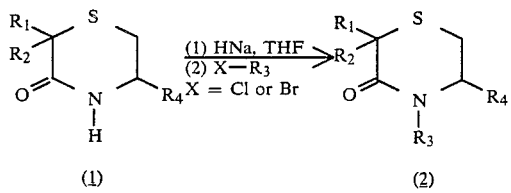

This method comprises treating, with an alkylating agent, $X—R_3$, the sodium salt (obtained by the action of sodium hydride in tetrahydrofuran) of thiamorpholinone (1), optionally substituted.

Generally the reaction is carried out at a temperature of about 50° C. under an inert atmosphere.

The compounds of Formula I wherein the radical $R_4 = H$ or alkyl and $R_3$ is other than hydrogen can also be obtained in accordance with the following reaction scheme:

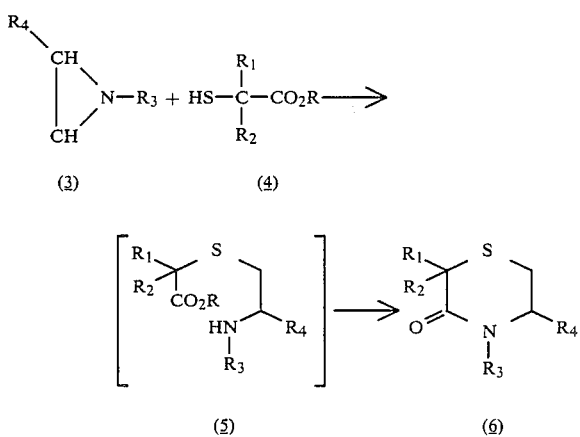

wherein the value of the various R's is alkyl containing 1–3 carbon atoms.

This method comprises reacting an aziridine (3) optionally substituted, with an α-mercapto ester (4) in a polar solvent, such as methanol or ethanol, at ambient temperature. After disappearance of the initial mercaptan, the mixture is held at the boil so as to effect or terminate the cyclization reaction. The solvent is removed by evaporation under vacuum and the N-substituted thiamorpholinone (6) thus obtained is purified either by distillation, or by recrystallization in an appropriate solvent.

The thiamorpholinone carboxylic acids ($R_4 = CO_2H$) can be obtained according to one of the two methods represented by the following reaction scheme:

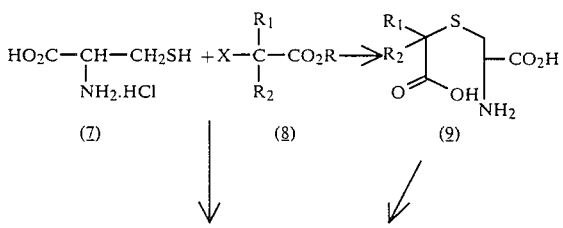

-continued

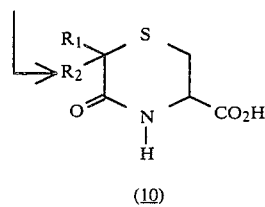

wherein the value of the various R's is alkyl containing 1–3 carbon atoms.

According to the first method, there is reacted in an alkaline medium (pH≃9) cysteine hydrochloride (7) with one equivalent of an α-halogenated ester (8), optionally mono- or disubstituted, in a hydroalcoholic polar medium, preferably at a temperature near 50° C., this temperature being maintained for a period of time of about 10 to 20 hours.

The mixture is then acidified to pH≃1 and concentrated under reduced pressure. The resulting thiamorpholinone carboxylic acid (10) is then extracted with chloroform and purified by recrystallization.

The second method of preparing thiamorpholinone carboxylic acids (10) uses, as the initial reactant, a S-(2-carboxyalkyl)cysteine (9), optionally mono- or disubstituted, which is cyclized by heating at an elevated temperature of about 170° C. in solution in o-dichlorobenzene until the theoretical quantity of water is removed.

Ths S-(2-carboxyalkyl)cysteines (9), optionally substituted, are known compounds which have been described in French Pat. Nos. 1,472,021 and 69,014,04.

The esters of the thiamorpholinone carboxylic acids, optionally mono- or disubstituted in the 2-position, are prepared by esterification of the thiamorpholinone carboxylic acids either by treating the sodium salt with an alkyl halide or by treating the acid directly with an esterification alcohol.

The compounds of Formula I wherein n=1, or sulfoxides, are prepared in accordance with known procedures by reacting at 0° C. one equivalent of $H_2O_2$ with a thiamorpholinone of Formula I wherein n=0 in the presence of an organic acid such as acetic or formic acid.

The following non-limiting examples are given to illustrate the invention.

EXAMPLE 1

2-methyl-1-oxo-3-thiamorpholinone (Compound 4)

To a solution of 9 g of 2-methyl-3-thiamorpholinone in a mixture of 50 cm³ of formic acid and 10 cm³ of acetic anhydride, cooled to 0° C., 7 cm³ of $H_2O_2$ at 110 vol. are slowly added. After an 18 hour reaction period, the solution is concentrated under reduced pressure. The resulting product is dissolved in chloroform and the chloroform solution is deposited on a silica gel column.

The expected sulfoxide is eluted with a 1:1 ethyl acetate-methanol mixture, then recrystallized in ethanol.

The resulting white crystals have a melting point of 136° C.

| Analysis: $C_5H_9NO_2S$ | | | | |
|---|---|---|---|---|
| Calculated: | C 40.78 | H 6.16 | N 9.52 | S 21.78 |

-continued

| Analysis: $C_5H_9NO_2S$ | | | | |
|---|---|---|---|---|
| Theoretical: | 40.91 | 6.31 | 9.45 | 21.85 |

EXAMPLE 2

2,2-dimethyl-1-oxo-3-thiamorpholinone (Compound 6)

This product is prepared, starting with 2,2-dimethyl-3-thiamorpholinone, in accordance with the procedures of Example 1. After two crystallizations in ethanol white crystals, whose melting point is 165° C., are obtained.

| Analysis: $C_6H_{11}NO_2S$ | | | | |
|---|---|---|---|---|
| Calculated: | C 44.70 | H 6.88 | N 8.69 | S 19.89 |
| Theoretical: | 44.63 | 6.90 | 8.86 | 20.12 |

EXAMPLE 3

3-thiamorpholinone-5-carboxylic acid (Compound 8)

A suspension of 179.5 g of S-carboxymethyl cysteine (1 mole) in 500 cm³ of o-dichlorobenzene, vigorously agitated under an inert atmosphere, is held at 170° C. The temperature of the oil bath is progressively elevated until the azeotropic water-orthodichlorobenzene mixture distills and the heating is maintained until the theoretical amount of water, which is 18 cm³, is removed.

The reaction mixture is then cooled and the resulting very colored solid is filtered, washed with hexane and then dried. The solid is then dissolved in 4.5 liters of methanol in the presence of animal charcoal. The mixture is filtered and the filtrate is then concentrated to about 1.5 liters, after which it is cooled to 0° C. On filtration and subsequent drying 115 g of beige crystals whose melting point is 188° C. are isolated.

| Analysis: $C_5H_7NO_3S$ | | | | | |
|---|---|---|---|---|---|
| Calculated: | C 37.26 | H 4.38 | N 8.69 | O 29.78 | S 19.89 |
| Theoretical: | 37.24 | 4.33 | 8.76 | 29.95 | 19.88 |

EXAMPLE 4

1-oxo-3-thiomorpholinone-5-carboxylic acid (Compound 9)

1 g of the 3-thiamorpholinone-5-carboxylic acid obtained in Example 3 is permitted to stand for 2 days at 0° C. in the following mixture: 15 cm³ of acetic acid, 3 cm³ of acetic anhydride, 10 cm³ of chloroform and 0.65 cm³ of $H_2O_2$.

After concentrating this reaction mixture, the expected sulfoxide crystallizes. It is filtered, then recrystallized in a 1:3 water-ethanol mixture, yielding 1 g of white crystals whose melting point is 180° C.

| Analysis: $C_5H_7NO_4S$ | | | | |
|---|---|---|---|---|
| Calculated: | C 33.89 | H 3.98 | N 7.91 | S 18.10 |
| Theoretical: | 33.73 | 4.04 | 7.98 | 18.00 |

EXAMPLE 5

2-methyl-3-thiamorpholinone-5-carboxylic acid (Compound 10)

To a solution heated to 60° C. of 52.65 g of cysteine hydrochloride in 200 cm³ of ethanol and 175 cm³ of water, stirred under an inert atmosphere, there is added a 5M solution of potash to adjust the pH to 9; this pH being maintained throughout the duration of the reaction. Then 40 g of 2-chloro ethyl propionate are slowly added.

After a 20 hour reaction period, the reaction mixture is acidified to pH=1 by the addition of HCl. The reaction medium is concentrated under reduced pressure and then chloroform extracted. The chloroformic phase is dried under calcium chloride and then concentrated.

The resulting 2-methyl-3-thiamorpholinone-5-carboxylic acid is recrystallized in an isopropyl ether-isopropyl alcohol mixture, yielding 20 g of white needles whose melting point is 185°-188° C.

| Analysis: $C_6H_9NO_3S$ | | | | |
|---|---|---|---|---|
| Calculated: | C 41.13 | H 5.18 | N 7.99 | S 18.30 |
| Theoretical: | 41.17 | 5.33 | 7.96 | 18.10 |

EXAMPLE 6

2-methyl-1-oxo-3-thiamorpholinone-5-carboxylic acid (Compound 11)

The oxidation is carried out as described in Example 4. There is obtained a yield of 50% of the expected sulfoxide, after recrystallization in ethanol, which is provided in the form of a white solid whose melting point is 194° C.

| Analysis: $C_6H_9NO_4S$ | | | | |
|---|---|---|---|---|
| Calculated: | C 37.70 | H 4.74 | N 7.33 | S 16.80 |
| Theoretical: | 37.43 | 4.85 | 7.23 | 16.81 |

EXAMPLE 7

2,2-dimethyl-3-thiamorpholinone-5-carboxylic acid (Compound 12)

To a mixture of 19.55 g of cysteine hydrochloride, 21.7 g of 2-bromo-2-methyl ethyl propionate in 125 cm³ of ethanol and 20 cm³ of water, stirred at ambient temperature under an inert atmosphere, there are slowly added 3 equivalents of 5N potash so as to maintain the pH at ≈9.

The mixture is then brought to a temperature of 50° C. After an 8 hour reaction period, the reaction is terminated and the pH is adjusted to 7 by the addition of HCl. On evaporation under vacuum, the alcohol is distilled off and the pH of the aqueous solution is adjusted to 1. From this solution, cooled to 0° C., 14 g of a solid crystallize, which solid is then recrystallized in an isopropyl ether-isopropyl alcohol mixture. The resulting white crystals have a melting point of 208° C.

| Analysis: $C_7H_{11}NO_3S$ | | | | |
|---|---|---|---|---|
| Calculated: | C 44.42 | H 5.85 | N 7.40 | S 16.94 |
| Theoretical: | 44.50 | 5.16 | 7.25 | 16.99 |

EXAMPLE 8

2,2-dimethyl-1-oxo-3-thiamorpholinone carboxylic acid (Compound 13)

To a solution, stirred at ambient temperature, of 14.2 g of 2,2-dimethyl-3-thiamorpholinone-5-carboxylic acid (obtained in Example 7) in a mixture of 76 cm$^3$ of formic acid and 17 cm$^3$ of acetic acid there is added one equivalent of $H_2O_2$. After 18 hours, the reaction being terminated, the reaction medium is concentrated under reduced pressure. The resulting solid is recrystallized in a water-ethanol mixture, yielding, after filtering and drying, 11 g of white crystals whose melting point is 212° C.

| Analysis: $C_7H_{11}NO_4S$ | | | | |
|---|---|---|---|---|
| Calculated: | C 40.97 | H 5.40 | N 6.83 | S 15.62 |
| Theoretical: | 40.92 | 5.37 | 7.08 | 15.74 |

EXAMPLE 9

4-(2-hydroxyethyl)-3-thiamorpholinone (Compound 14)

To a solution, stirred at ambient temperature, of 120 g of ethyl thioglycolate (1 mole) in 300 cm$^3$ of absolute ethanol, placed under an inert atmosphere, there is slowly added a solution of 87 g (1 mole) of N-(2-hydroxyethyl)aziridine diluted in 100 cm$^3$ of ethanol. The reaction is exothermic and the temperature of the reaction mixture is maintained at a temperature lower than 50° C. One half hour after the end of the introduction, the solution is brought to reflux for 6 hours.

The ethanol is then removed and the resulting liquid is distilled under reduced pressure.

BP/0.1–0.3 mm=167°–170° C.

The 4-(2-hydroxyethyl)-3-thiamorpholinone is a light yellow, viscous and hygroscopic liquid whose elemental analysis under the hydrated form is as follows:

| Analysis: $C_6H_{11}NO_2S.0.25H_2O$ | | | | | |
|---|---|---|---|---|---|
| Calculated: | C 43.48 | H 6.99 | N 8.45 | O 21.73 | S 19.35 |
| Theoretical: | 43.37 | 6.96 | 8.44 | 21.37 | 19.36 |

EXAMPLE 10

4-(2-hydroxyethyl)-1-oxo-3-thiamorpholinone (Compound 15)

This sulfoxide is prepared by reacting, for a week, one equivalent of $H_2O_2$ with 4-(2-hydroxyethyl) 3-thiamorpholinone (obtained in Example 9) solubilized at 0° C. in an acetic acid-acetic anhydride mixture. After concentration of the mixture the resulting liquid is solubilized in a minimum of an isopropyl ether-isopropyl alcohol mixture. Starting with this solution, placed at −25° C., white crystals whose melting point is 45° C. are isolated.

| Analysis: $C_6H_{11}NO_3S$ | | | | |
|---|---|---|---|---|
| Calculated: | C 40.66 | H 6.26 | N 7.80 | S 18.08 |
| Theoretical: | 40.73 | 6.28 | 7.73 | 18.16 |

EXAMPLE 11

4-(2,3-dihydroxy)-3-thiamorpholinone (Compound 17)

To the sodium salt of 3-thiomorpholinone, prepared by reacting the latter with sodium hydride in tetrahydrofuran brought to the boil, there are added, after cooling, 1.1 equivalents of epichlorohydrin. The reaction mixture is then held for 4 hours at 50° C. After cooling the same, the reaction mixture is filtered, concentrated and deposited on a silica gel column.

The 4-(2,3-epoxypropyl)-3-thiamorpholinone is eluted with a 1:1 ethyl acetate-methanol mixture. After concentration of the elution phases and verification of the structure, the epoxide is hydrolyzed, in the water bath, with an aqueous solution in the presence of a few drops of HCl. After verification in C.C.M. of the total transformation of the 4-(2,3-epoxypropyl)-3-thiamorpholinone into 4-(2,3-dihydroxypropyl)-3-thiamorpholinone, the solution is concentrated under reduced pressure. The resulting yellow colored liquid is dried in a dessicator and the expected structure confirmed by mass spectrography: molecular ion m/e:191 (base peak m/e:102).

EXAMPLE 12

3-thiamorpholinone-5-n-octyl carboxylate (Compound 18)

Method A

Initially the sodium salt of 3-thiamorpholinone-5-carboxylic acid, obtained in Example 4, is prepared by bringing a mixture of 3.2 g of this acid (0.02 mole) and 1 g of sodium carbonate (0.01 mole) in 20 cm$^3$ of dimethylformamide (DMF) to a temperature of about 70° C.

After a few minutes, the mixture is homogeneous and there are added thereto 3.8 g of n-octyl bromide (0.02 mole). Then the temperature of the reaction mixture is raised to 120° C. for one hour. After cooling, the resulting sodium bromide is filtered. The filtrate is then concentrated under reduced pressure. The resulting liquid is stirred into a 95:5 mixture of methylene chloride-ethyl acetate in the presence of silica gel so as to eliminate the colored impurities. After filtration, the solution is concentrated under vacuum and the expected product crystallizes, yielding 5 g of a pasty solid whose melting point is 45° C.

| Analysis: $C_{13}H_{23}NO_3S$ | | | | |
|---|---|---|---|---|
| Calculated: | C 57.11 | H 8.48 | N 5.12 | S 11.73 |
| Theoretical: | 57.10 | 8.43 | 5.12 | 11.79 |

Method B

A stirred mixture of 9 g of S-carboxymethyl cysteine (0.05 mole) in an excess of n-octanol (0.1 mole), under an inert atmosphere, is heated to a temperature of 170° C. for 2 hours.

After cooling, the mixture is dissolved in a minimum of toluene. The resulting solution is deposited on a silica gel column and then eluted using a 95:5 methylenechloride-ethyl acetate mixture.

After concentration of the elution phases, the expected ester is obtained, this ester having characteristics which are identical to those of the ester obtained in accordance with Method A, above.

EXAMPLES 13 to 18

In accordance with the same operating procedures as those in Method B of Example 12 and by using the same amounts of reactants, the following esters have been obtained:

EXAMPLE 13

3-thiamorpholinone-5-n-decyl carboxylate (Compound 19)

Starting with n-decyl alcohol, pasty beige crystals whose melting point is 48° C. are obtained:

| Analysis: $C_{15}H_{27}NO_3S$ | | | | |
|---|---|---|---|---|
| Calculated: | C 59.77 | H 9.03 | N 4.65 | S 10.64 |
| Theoretical: | 59.90 | 9.01 | 4.60 | 10.66 |

EXAMPLE 14

3-thiamorpholinone-5-n-dodecyl carboxylate (Compound 20)

Starting with n-dodecanol, an amorphous beige solid whose melting point is 50° C. is obtained.

| Analysis: $C_{17}H_{31}NO_3S$ | | | | |
|---|---|---|---|---|
| Calculated: | C 61.97 | H 9.48 | N 4.25 | S 9.73 |
| Theoretical: | 61.75 | 9.48 | 4.28 | 9.87 |

EXAMPLE 15

3-thiamorpholinone-5-(2-ethylhexyl)carboxylate (Compound 21)

Starting with 2-ethyl hexanol, a colorless liquid is obtained which is then purified by chromatography on silica gel.

| Analysis: $C_{13}H_{22}NO_3S$ | | | | |
|---|---|---|---|---|
| Calculated: | C 57.11 | H 8.43 | N 5.12 | S 11.73 |
| Theoretical: | 56.96 | 8.53 | 4.99 | 11.68 |

EXAMPLE 16

3-thiamorpholinone-5-n-tetradecyl carboxylate (Compound 22)

Starting with n-tetradecanol crystals are obtained which are purified initially by chromatography on silica gel, then by recrystallization in petroleum ether.

The expected ester is provided in the form of a beige solid whose melting point is 66° C.

| Analysis: $C_{19}H_{35}NO_3S$ | | | | |
|---|---|---|---|---|
| Calculated: | C 63.92 | H 9.87 | N 3.97 | S 8.97 |
| Theoretical: | 64.04 | 9.86 | 3.89 | 8.94 |

EXAMPLE 17

3-thiamorpholinone-5-n-hexadecyl carboxylate (Compound 23)

Starting with n-hexadecanol, the desired ester is obtained which is then purified by chromatography on silica gel. After concentration of the elution phases, the ester is provided in the form of a white powder whose melting point is 75° C.

| Analysis: $C_{21}H_{39}NO_3S$ | | | | |
|---|---|---|---|---|
| Calculated: | C 65.40 | H 10.19 | N 3.65 | S 8.31 |
| Theoretical: | 65.50 | 10.12 | 3.59 | 8.29 |

EXAMPLE 18

3-thiamorpholinone-5-(2,3-dihydroxy)propyl carboxylate (Compound 25)

This product is prepared in accordance with Method A of Example 12.

The sodium salt of 3-thiamorpholinone-5-carboxylic acid in DMF is treated with one equivalent of 3-chloro-1,2-propanediol for 8 hours at 120° C.

After cooling, the insolubles are filtered off and the filtrate is concentrated under reduced pressure. The resulting liquid is treated with animal charcoal in methanol. After filtration, the methanolic phase is concentrated and the resulting desired product is purified by passage through silica gel and eluted with a 9:1 ethyl acetate:methanol mixture.

After concentration of the elution phases there is obtained a very viscous liquid having a yellow color whose R.M.N. and mass spectra correspond to the expected structure (molecular ion at m/e:235 base peak at m/e:116).

EXAMPLE 19

4-(ethoxycarbonylmethyl)-3-thiamorpholinone (Compound 26)

To a solution of 5 g of 3-thiamorpholinone in 100 cm$^3$ of anhydrous tetrahydrofuran, stirred out of contact with the humidity of the air, there are added 1.1 equivalents of sodium hydride. The resulting mixture is held at reflux for one hour.

There are then slowly added, at ambient temperature, 1.1 equivalents of ethyl chloroacetate. The reaction mixture is then brought to 50° C. for one hour at which point the mineral salts are filtered off and washed with THF. The filtrate is concentrated under reduced pressure and the residue is then dissolved in a minimum of methylene chloride to remove any remaining traces of sodium chloride. The methylene chloride phase is filtered and the solvent rectified under vacuum.

The 4-(ethoxycarbonylmethyl)-3-thiamorpholinone is a yellow colored liquid at ambient temperature.

| Analysis: $C_8H_{13}NO_3S.0.25H_2O$ | | | | | |
|---|---|---|---|---|---|
| Calculated: | C 46.27 | H 6.50 | N 6.75 | O 25.06 | S 15.42 |
| Theoretical: | 46.38 | 6.43 | 6.81 | 25.09 | 15.46 |

EXAMPLE 20

4-(carboxymethyl)-3-thiamorpholinone (Compound 30)

To a solution of 2 g of the ester of Example 19 in 50 cm$^3$ of ethanol, there are added 1.1 equivalents of alcoholic potash.

The mixture is held for one hour under agitation at the boil. After cooling, the crystallized potassium salt is filtered, washed with a little pure ethanol and dried.

1.68 g of salt are obtained which are then stirred in suspension in isopropanol to which is added the stoichiometric amount of HCl acid in solution in isopropanol.

After one hour, the mixture is filtered. The filtrate is then concentrated under reduced pressure. The expected acid is dissolved hot in 1,2-dichloroethane. Then the resulting solution is filtered in order to remove any traces of potassium chloride and the solvent is rectified under reduced pressure, yielding 1.30 g of 4-(carboxymethyl)-3-thiamorpholinone in the form of beige colored crystals whose melting point is 138° C.

| Analysis: $C_6H_9NO_3S$ | | | | | |
|---|---|---|---|---|---|
| Calculated: | C 41.14 | H 5.14 | N 8.00 | O 27.43 | S 18.29 |
| Theoretical: | 41.11 | 5.15 | 8.04 | 27.50 | 18.26 |

EXAMPLE 21

4-(carbamylmethyl)-3-thiamorpholinone (Compound 33)

The reaction is carried out as in the case of the preparation of 4-(ethoxy carbonylmethyl)-3-thiamorpholinone (Example 19) by replacing ethyl chloroacetate with chloroacetamide.

At the end of the reaction the anticipated product is purified initially by crystallization in ethylacetate and then by washing the expected crystals with acetone.

The 4-(carbamylmethyl)-3-thiamorpholinone is a white solid whose melting point is 145° C.

| Analysis: $C_6H_{10}N_2O_2S$ | | | | | |
|---|---|---|---|---|---|
| Calculated: | C 41.38 | H 5.75 | N 16.09 | O 18.36 | S 18.40 |
| Theoretical: | 41.40 | 5.81 | 16.11 | 18.50 | 18.33 |

EXAMPLE 22

Softening and hydrating makeup base

| | |
|---|---|
| Self-emulsifiable glycerol stearate | 3.00 g |
| Cetyl alcohol | 0.50 g |
| Stearyl alcohol | 0.50 g |
| Petrolatum oil | 13.00 g |
| Sesame oil | 10.00 g |
| Stearic acid | 3.00 g |
| 2-methyl-3-thiamorpholinone | 5.00 g |
| Methyl parahydroxybenzoate | 0.30 g |
| Antioxidant-perfume, sufficient amounts of each | |
| Sterile demineralized water, sufficient amount for | 100.00 g |

EXAMPLE 23

Softening and hydrating body milk

| | |
|---|---|
| Sorbitan sesquioleate | 2.00 g |
| Oxyethylenated glycerol stearate | 2.00 g |
| Cetyl alcohol | 1.00 g |
| Petrolatum oil | 10.00 g |
| 4-(2-hydroxyethyl)-3-thiamorpholinone | 10.00 g |
| Perfume | 1.00 g |
| Methyl parahydroxybenzoate | 0.30 g |
| Sterile demineralized water, sufficient amount for | 100.00 g |

EXAMPLE 24

Ampoule for treatment of the face

| | |
|---|---|
| Pure gelatin in flake form | 2.00 g |
| 3-thiamorpholinone | 20.00 g |
| Methyl parahydroxybenzoate | 0.10 g |
| Imidazoline/urea copolymer sold under the tradename "Germall 115" by Sutton | 0.30 g |
| Perfume | 0.20 g |
| Sterile demineralized water, sufficient amount for | 100.00 g |

EXAMPLE 25

Hydrating mask for dry skin

| | |
|---|---|
| Carboxyvinyl polymer (Carbopol 940 sold by Goodrich) | 0.75 g |
| Soda | 0.30 g |
| 4-(2-hydroxyethyl)-3-thiamorpholinone | 0.20 g |
| Glycerine | 2.00 g |
| Propylene glycol | 3.00 g |
| Perfume, sufficient amount | |
| Demineralized water, sufficient amount for | 100.00 g |

EXAMPLE 26

Hydrating lotion

| | |
|---|---|
| 3-thiamorpholinone-5-carboxylic acid | 15.00 g |
| Polyethylene glycol | 1.00 g |
| Allantoin | 0.05 g |
| Buffer, amount sufficient for pH 7 | |
| Methyl parahydroxybenzoate | 0.10 g |
| Propyl parahydroxybenzoate | 0.05 g |
| Perfume, sufficient amount | |
| Sterile demineralized water, sufficient amount for | 100.00 g |

EXAMPLE 27

Makeup remover cream

| | |
|---|---|
| Polyoxyethylenated cetyl ether | 2.00 g |
| Cetyl alcohol | 1.00 g |
| Self-emulsifiable glycerol stearate | 2.00 g |
| Mineral oil | 18.00 g |
| Isopropyl myristate | 5.00 g |
| Lanolin | 3.00 g |
| Carboxyvinylpolymer (Carbopol 941 sold by Goodrich) | 0.40 g |
| Triethanolamine | 0.40 g |
| Methyl parahydroxybenzoate | 0.30 g |
| 3-thiamorpholinone-5-carboxylic acid | 5.00 g |
| Perfume | 0.30 g |
| Demineralized water, sufficient amount for | 100.00 g |

EXAMPLE 28

Care cream in the form of a hydrating water-in-oil emulsion

| | |
|---|---|
| Sorbitan sesquioleate | 3.00 g |
| Mineral oil | 17.00 g |
| Isopropyl myristate | 10.00 g |
| Extract of lanolin alcohols (Amerchol L101, sold by Amerchol) | 5.00 g |
| Petrolatum | 15.00 g |
| Methyl parahydroxybenzoate | 0.30 g |
| 3-thiamorpholinone | 0.50 g |

-continued

| | |
|---|---|
| Perfume | 0.30 g |
| Sterile demineralized water, sufficient amount for | 100.00 g |

EXAMPLE 29

Care cream in the form of a hydrating oil-in-water emulsion

| | |
|---|---|
| Polyoxyethylenated stearyl ether | 2.00 g |
| Polyoxyethylenated cetyl ether | 2.00 g |
| Self-emulsifiable glycerol monostearate | 4.00 g |
| Perhydrosqualene | 10.00 g |
| Mineral oil | 15.00 g |
| Stearic acid | 2.00 g |
| Carboxyvinyl polymer (Carbopol 941) | 0.40 g |
| Triethanolamine | 0.40 g |
| Perfume | 0.30 g |
| Methyl parahydroxybenzoate | 0.30 g |
| 4-(2-hydroxyethyl)-3-thiamorpholinone | 2.00 g |
| Demineralized water, sufficient amount for | 100.00 g |

EXAMPLE 30

Hydrating face cream

| | |
|---|---|
| Sorbitan monostearate oxyethylenated with 20 moles of ethylene oxide | 1.00 g |
| Cetyl alcohol | 1.00 g |
| Perhydrosqualene | 10.00 g |
| Virgin sesame oil | 5.00 g |
| Stearic acid | 2.00 g |
| 4-(2-hydroxyethyl)-3-thiamorpholinone | 3.00 g |
| 3-thiamorpholinone | 3.00 g |
| Preservative | 0.30 g |
| Antioxidant, sufficient amount | |
| Perfume, sufficient amount | |
| Demineralized water, sufficient amount for | 100.00 g |

EXAMPLE 31

Hydrating sunscreen cream for the face

| | |
|---|---|
| Magnesium lanolate | 3.4 g |
| Lanolin alcohol | 2.8 g |
| Perhydrosqualene | 15.00 g |
| Isopropyl myristate | 10.00 g |
| Virgin sesame oil | 10.00 g |
| Petrolatum oil | 8.8 g |
| 4-(2-hydroxyethyl)-3-thiamorpholinone | 3.00 g |
| 3-benzylidene camphor | 3.00 g |
| Preservative, sufficient amount | |
| Perfume, sufficient amount | |
| Antioxidant, sufficient amount | |
| Demineralized water, sufficient amount for | 100.00 g |

EXAMPLE 32

After-sun hydrating fluid emulsion

| | |
|---|---|
| Polyoxyethylenated stearate (sold under the tradename "Myrj 49" by Atlas | 0.8 g |
| Self-emulsifiable glycerol stearate | 1.2 g |
| Stearyl alcohol | 1.00 g |
| Petrolatum oil | 8.00 g |
| Soy oil | 3.00 g |
| Lanolin alcohol | 3.00 g |
| 4-(2-hydroxy propyl)-3-thiamorpholinone | 10.00 g |
| Antioxidant, sufficient amount | |
| Perfume, sufficient amount | |
| Preservative, sufficient amount | |

-continued

| | |
|---|---|
| Demineralized water, sufficient amount for | 100.00 g |

EXAMPLE 33

Hydrating handcream

| | |
|---|---|
| Cetyl ether polyoxyethylenated with 10 moles of ethylene oxide | 2.00 g |
| Self-emulsifiable glycerol stearate | 2.00 g |
| Cetyl alcohol | 1.00 g |
| Petrolatum oil | 5.00 g |
| Isopropyl myristate | 5.00 g |
| Lanolin | 3.00 g |
| 4-(2,3-dihydroxypropyl)-3-thiamorpholinone | 6.00 g |
| Methyl parahydroxybenzoate | 0.3 g |
| Perfume | 0.3 g |
| Demineralized water, sufficient amount for | 100.00 g |

EXAMPLE 34

Hydrating nourishing night cream

| | |
|---|---|
| Magnesium lanolate | 3.4 g |
| Lanolin alcohol | 2.8 g |
| Perhydrosqualene | 20.00 g |
| Isopropyl myristate | 5.00 g |
| Virgin sesame oil | 10.00 g |
| Petrolatum oil | 8.8 g |
| Methyl parahydroxybenzoate | 0.3 g |
| Perfume | 0.3 g |
| 4-(2-hydroxyethyl)-1-oxo-3-thiamorpholinone | 3.00 g |
| Poly-tissular extract | 2.00 g |
| Sterile demineralized water, sufficient amount for | 100.00 g |

EXAMPLE 35

Hydrating colored cream

| | |
|---|---|
| Magnesium lanolate | 4.25 g |
| Lanolin alcohol | 4.25 g |
| Paraffin oil | 30.5 g |
| Purcellin oil | 4.00 g |
| Ozokerite | 3.00 g |
| 3-thiamorpholinone-5-2-ethylhexyl carboxylate | 5.00 g |
| Silicone oil | 2.00 g |
| Iron oxide + titanium oxide | 4.00 g |
| Methyl parahydroxybenzoate | 0.3 g |
| Demineralized water, sufficient amount for | 100.00 g |

What is claimed is:

1. A process for imparting suppleness and elasticity to the skin comprising applying to the skin in an amount effective to impart suppleness and elasticity to said skin, a cosmetic composition containing 0.1 to 20 weight percent of a humectant, said humectant being a compound of the formula

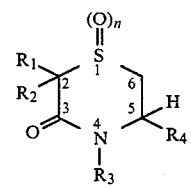

wherein

R₁ and R₂ each independently represent hydrogen or lower alkyl having 1-14 carbon atoms, R₃ represents hydrogen, linear or branched lower alkyl having 1-4 carbon atoms, mono- or polyhydroxyalkyl having 2-16 carbon atoms, carbamylalkyl, carboxyalkyl or alkoxycarbonylalkyl, wherein the alkyl moiety of each has 1-17 carbon atoms and the alkoxy moiety has 1-3 carbon atoms, R₄ represents hydrogen, lower alkyl having 1-4 carbon atoms or —COOR₅ wherein R₅ represents hydrogen, alkyl having 1-18 carbon atoms, alkyl having 1-18 carbon atoms and interrupted by one or more heteroatoms, or mono- or polyhydroxyalkyl having 2-18 carbon atoms, and n is 0 or 1.

2. The process of claim 1 wherein said compound is selected from the group consisting of
(1) 3-thiamorpholinone,
(2) 1-oxo-3-thiamorpholinone,
(3) 2-methyl-3-thiamorpholinone,
(4) 2-methyl-1-oxo-3-thiamorpholinone,
(5) 2,2-dimethyl-3-thiamorpholinone,
(6) 2,2-dimethyl-1-oxo-3-thiamorpholinone,
(7) 4-ethyl-3-thiamorpholinone,
(8) 3-thiamorpholinone-5-carboxylic acid,
(9) 1-oxo-3-thiamorpholinone-5-carboxylic acid,
(10) 2-methyl-3-thiamorpholinone-5-carboxylic acid,
(11) 2-methyl-1-oxo-3-thiamorpholinone-5-carboxylic acid,
(12) 2,2-dimethyl-3-thiamorpholinone-5-carboxylic acid,
(13) 2,2-dimethyl-1-oxo-3-thiamorpholinone-5-carboxylic acid,
(14) 4-(2-hydroxyethyl)-3-thiamorpholinone,
(15) 4-(2-hydroxyethyl)-1-oxo-3-thiamorpholinone,
(16) 4-(2-hydroxypropyl)-3-thiamorpholinone,
(17) 4-(2,3-dihydroxypropyl)-3-thiamorpholinone,
(18) 3-thiamorpholinone-5-n-octyl carboxylate,
(19) 3-thiamorpholinone-5-n-decyl carboxylate,
(20) 3-thiamorpholinone-5-n-dodecyl carboxylate,
(21) 3-thiamorpholinone-5-(2-ethyl)hexyl carboxylate,
(22) 3-thiamorpholinone-5-n-tetradecyl carboxylate,
(23) 3-thiamorpholinone-5-n-hexadecyl carboxylate,
(24) 3-thiamorpholinone-5-(2-hydroxy)propyl carboxylate,
(25) 3-thiamorpholinone-5-(2,3-dihydroxy)propyl carboxylate,
(26) 4-(ethoxycarbonylmethyl)-3-thiamorpholinone,
(27) 4-(methoxycarbonylmethyl)-3-thiamorpholinone,
(28) 4-(2-ethoxycarbonylethyl)-3-thiamorpholinone,
(29) 4-(1-ethoxycarbonylethyl)-3-thiamorpholinone,
(30) 4-(carboxymethyl)-3-thiamorpholinone,
(31) 4-(2-carboxyethyl)-3-thiamorpholinone,
(32) 4-(1-carboxyethyl)-3-thiamorpholinone, and
(33) 4-(carbamylmethyl)-3-thiamorpholinone.

3. The process of claim 1 wherein said compound is present in an amount ranging from 2 to 12 weight percent based on the total weight of said composition.

* * * * *